(12) United States Patent
Cabrera (10) Patent No.: US 11,452,510 B2
(45) Date of Patent: *Sep. 27, 2022

(54) ADAPTER ASSEMBLIES FOR SURGICAL DEVICES

(71) Applicant: Covidien LP, Mansfield, MA (US)

(72) Inventor: Ramiro Cabrera, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 220 days.

This patent is subject to a terminal disclaimer.

(21) Appl. No.: 16/807,373

(22) Filed: Mar. 3, 2020

(65) Prior Publication Data
US 2020/0222062 A1     Jul. 16, 2020

Related U.S. Application Data

(63) Continuation of application No. 15/493,788, filed on Apr. 21, 2017, now Pat. No. 10,588,610.
(Continued)

(51) Int. Cl.
*A61B 17/072* (2006.01)
*A61B 17/00* (2006.01)
(Continued)

(52) U.S. Cl.
CPC ........ *A61B 17/00* (2013.01); *A61B 17/07207* (2013.01); *A61B 17/1155* (2013.01);
(Continued)

(58) Field of Classification Search
CPC ................ A61B 17/068; A61B 17/072; A61B 17/07207; A61B 17/115; A61B 17/00234;
(Continued)

(56) References Cited

U.S. PATENT DOCUMENTS

| 2,777,340 A | 1/1957 | Hettwer et al. |
| 2,957,353 A | 10/1960 | Babacz |

(Continued)

FOREIGN PATENT DOCUMENTS

| CA | 2451558 A1 | 1/2003 |
| CN | 1547454 A | 11/2004 |

(Continued)

OTHER PUBLICATIONS

Extended European Search Report corresponding to International Application No. EP 14 18 4882.0 dated May 12, 2015.
(Continued)

*Primary Examiner* — Scott A Smith
(74) *Attorney, Agent, or Firm* — Carter, DeLuca & Farrell LLP (57) ABSTRACT

An adapter assembly for connecting an end effector to an actuation assembly includes a base member defining a plurality of notches spaced at least partially about a circumference of the base member, a handle supported on the base member and rotatable about a longitudinal axis of the base member, and a latch mechanism supported on the handle assembly and selectively engageable with the base member. The latch mechanism includes a button member and a locking member. The button member is movable between a first position in which the locking member is received within one of the plurality of notches to lock the handle relative to the base member, and a second position in which the locking member is spaced from the plurality of notches to unlock the handle relative to the base member.

20 Claims, 7 Drawing Sheets

Related U.S. Application Data (60) Provisional application No. 62/333,976, filed on May 10, 2016.

(51) Int. Cl.

| | |
|---|---|
| *A61B 17/115* | (2006.01) |
| *A61B 17/29* | (2006.01) |
| *A61B 17/16* | (2006.01) |
| *A61C 8/00* | (2006.01) |
| *A61B 90/00* | (2016.01) |

(52) U.S. Cl.
CPC ...... *A61B 17/1615* (2013.01); *A61B 17/2909* (2013.01); *A61C 8/0089* (2013.01); *A61B 17/00234* (2013.01); *A61B 17/072* (2013.01); *A61B 17/1635* (2013.01); *A61B 17/1673* (2013.01); *A61B 2017/0046* (2013.01); *A61B 2017/00371* (2013.01); *A61B 2017/00398* (2013.01); *A61B 2017/00464* (2013.01); *A61B 2017/00473* (2013.01); *A61B 2017/00482* (2013.01); *A61B 2017/00862* (2013.01); *A61B 2017/07214* (2013.01); *A61B 2017/07257* (2013.01); *A61B 2017/07271* (2013.01); *A61B 2017/291* (2013.01); *A61B 2017/2927* (2013.01); *A61B 2017/2929* (2013.01); *A61B 2090/062* (2016.02); *A61B 2090/0813* (2016.02)

(58) Field of Classification Search
CPC ...... A61B 17/2909; A61B 2017/07214; A61B 2017/00017; A61B 2017/00398; A61B 2017/07271; A61B 2017/00477; A61B 2017/2927; A61B 2017/2929; A61B 2017/0046
USPC .............. 227/19, 175.1, 175.2, 176.1, 180.1; 606/1, 139, 153, 219
See application file for complete search history.

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,409,866 A * | 10/1983 | McBride ................. B25G 1/04 | |
| | | | 16/429 |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,314,424 A * | 5/1994 | Nicholas ............ A61B 17/2909 | |
| | | | 606/1 |
| 5,326,013 A | 7/1994 | Green et al. | |
| 5,330,502 A * | 7/1994 | Hassler ................. A61B 17/29 | |
| | | | 600/564 |
| 5,344,428 A * | 9/1994 | Griffiths ................ A61B 17/29 | |
| | | | 600/564 |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,441,494 A * | 8/1995 | Ortiz ........................... B25J 3/00 | |
| | | | 294/213 |
| 5,464,300 A * | 11/1995 | Crainich .............. A61B 17/068 | |
| | | | 403/322.1 |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,586,830 A * | 12/1996 | Wanek .................. A47B 23/025 | |
| | | | 108/146 |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,702,408 A * | 12/1997 | Wales ............... A61B 17/07207 | |
| | | | 606/139 |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,820,009 A | 10/1998 | Melling et al. | |
| 5,823,066 A * | 10/1998 | Huitema .......... A61B 17/07207 | |
| | | | 74/527 |
| 5,863,159 A | 1/1999 | Lasko | |
| 5,908,427 A | 6/1999 | McKean et al. | |
| 5,921,956 A * | 7/1999 | Grinberg ............. A61B 1/0052 | |
| | | | 604/95.01 |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,039,126 A * | 3/2000 | Hsieh ....................... B25B 21/00 | |
| | | | 173/170 |
| 6,045,560 A | 4/2000 | McKean et al. | |
| 6,090,123 A | 7/2000 | Culp et al. | |
| 6,126,633 A * | 10/2000 | Kaji .................. A61M 25/0084 | |
| | | | 604/164.01 |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |

(56) References Cited

U.S. PATENT DOCUMENTS

| | | |
|---|---|---|
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |

(56) References Cited

U.S. PATENT DOCUMENTS

| | | |
|---|---|---|
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,314,916 B2 * | 4/2016 | Tsuchiya ................ A01G 3/053 |
| 10,588,610 B2 * | 3/2020 | Cabrera ............ A61B 17/1155 |
| 10,751,058 B2 * | 8/2020 | Cabrera ............ A61B 17/1155 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2003/0216618 A1 * | 11/2003 | Arai ........................ A61B 1/07 |
| | | 600/178 |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0006432 A1 * | 1/2005 | Racenet ............ A61B 17/068 |
| | | 227/176.1 |
| 2005/0125027 A1 | 6/2005 | Knodel et al. |
| 2005/0131442 A1 | 6/2005 | Yachia et al. |
| 2006/0020241 A1 * | 1/2006 | Piskun ............ A61B 17/3403 |
| | | 604/93.01 |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0249497 A1 | 9/2010 | Peine et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0025492 A1 * | 2/2012 | Grintz ..................... B62B 7/08 |
| | | 280/647 |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |

(56) References Cited

U.S. PATENT DOCUMENTS

| | | |
|---|---|---|
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0155923 A1* | 6/2014 | Edwards ............... A61B 90/90 606/170 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| CN | 106388877 A | 2/2017 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 3123960 A1 | 2/2017 |
| ES | 2333509 A1 | 2/2010 |
| JP | 2005125075 A | 5/2005 |
| KR | 20120022521 A | 3/2012 |
| WO | 2011108840 A2 | 9/2011 |
| WO | 2012/040984 A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.

(56) References Cited

OTHER PUBLICATIONS

Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report corresponding to EP 15 184 915.5-1654 dated Sep. 16, 2016.
European Search Report dated Oct. 13, 2017, issued in EP Application No. 17170078.
Chinese Office Action (with English translation) dated Oct. 10, 2020, corresponding to counterpart Chinese Application No. 201710321843.3; 16 total pages.
Chinese Office Action dated May 19, 2021, issued in corresponding CN Appln. No. 201710321843, 10 pages.
English translation of Chinese Decision of Rejection dated Nov. 2, 2021, corresponding to counterpart Chinese Application No. 201710321843.5; 1 page.

* cited by examiner

ADAPTER ASSEMBLIES FOR SURGICAL DEVICES

CROSS-REFERENCE TO RELATED APPLICATIONS

This application is a continuation of U.S. application Ser. No. 15/493,788, filed Apr. 21, 2017, now U.S. Pat. No. 10,588,610, and claims the benefit of and priority to U.S. Provisional Patent Application Ser. No. 62/333,976, filed May 10, 2016, the entire disclosures each of which are incorporated by reference herein.

BACKGROUND

The present disclosure relates generally to adapter assemblies for selectively connecting end effectors to the actuation units of powered surgical devices. More specifically, the present disclosure relates to a latch mechanism for rotationally securing a rotation handle of the powered surgical devices relative to the actuation assemblies.

BACKGROUND OF RELATED ART

Powered devices for use in surgical procedures typically convert rotational motion from an actuation assembly to linear motion for effectuating one or more functions, e.g., clamping, stapling, cutting. To permit rotational alignment of an end effector attached to the actuation assembly without the operator having to manipulate the actuation assembly in an uncomfortable or awkward position, adapter assemblies have been developed for enabling selective rotation of the end effector relative to the actuation assembly. Such adapter assemblies generally include a base that is fixedly secured to the actuation assembly and a rotation handle to which an end effector is attached for rotating the end effector relative to the base and the actuation assembly. It would be beneficial to provide an adapter assembly with a latch assembly to permit the selective rotation of the rotation handle relative to the base.

SUMMARY

Accordingly, an adapter assembly for operably connecting an end effector to an actuation assembly is provided. The adapter assembly includes a base member configured for operable connection to an actuation assembly, a handle assembly supported on the base member and rotatable about a longitudinal axis of the base member, and a latch mechanism supported on the handle assembly and selectively engageable with the base member. The base member defines a plurality of notches spaced at least partially about a circumference of the base member. The latch mechanism includes a button member and a locking member extending from the button member. The locking member is movable between a first position in which the locking member is received within one of the plurality of notches to rotationally lock the handle assembly relative to the base member, and a second position in which the locking member is spaced from the plurality of notches to unlock the handle assembly relative to the base member.

In embodiments, the base member includes a distal annular flange extending at least partially about the circumference of the base member and defining the plurality of notches. The locking member may define a notch that aligns with the distal annular flange when the locking member is in the second position. The button member may be positioned on a radially outer surface of the handle assembly. The latch mechanism may include a biasing member for biasing the button member radially outward. The biasing member may be a compression spring. The latch mechanism may include a biasing member for biasing the locking member. The biasing member may be a leaf spring. The button member may include indicia for indicating the direction of rotation of the handle assembly relative to the base member.

In embodiments, the plurality of notches is spaced at regular intervals about the circumference of the base member. The plurality of notches may include a first notch and a second notch disposed one-hundred eighty degrees (180°) opposite the first notch. The plurality of notches may include a third notch disposed between the first and second notches. The third notch may be disposed ninety degrees (90°) relative to the first notch. The locking member may be pivotally secured to the button member.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed adapter assembly for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

Figures 1, 2:
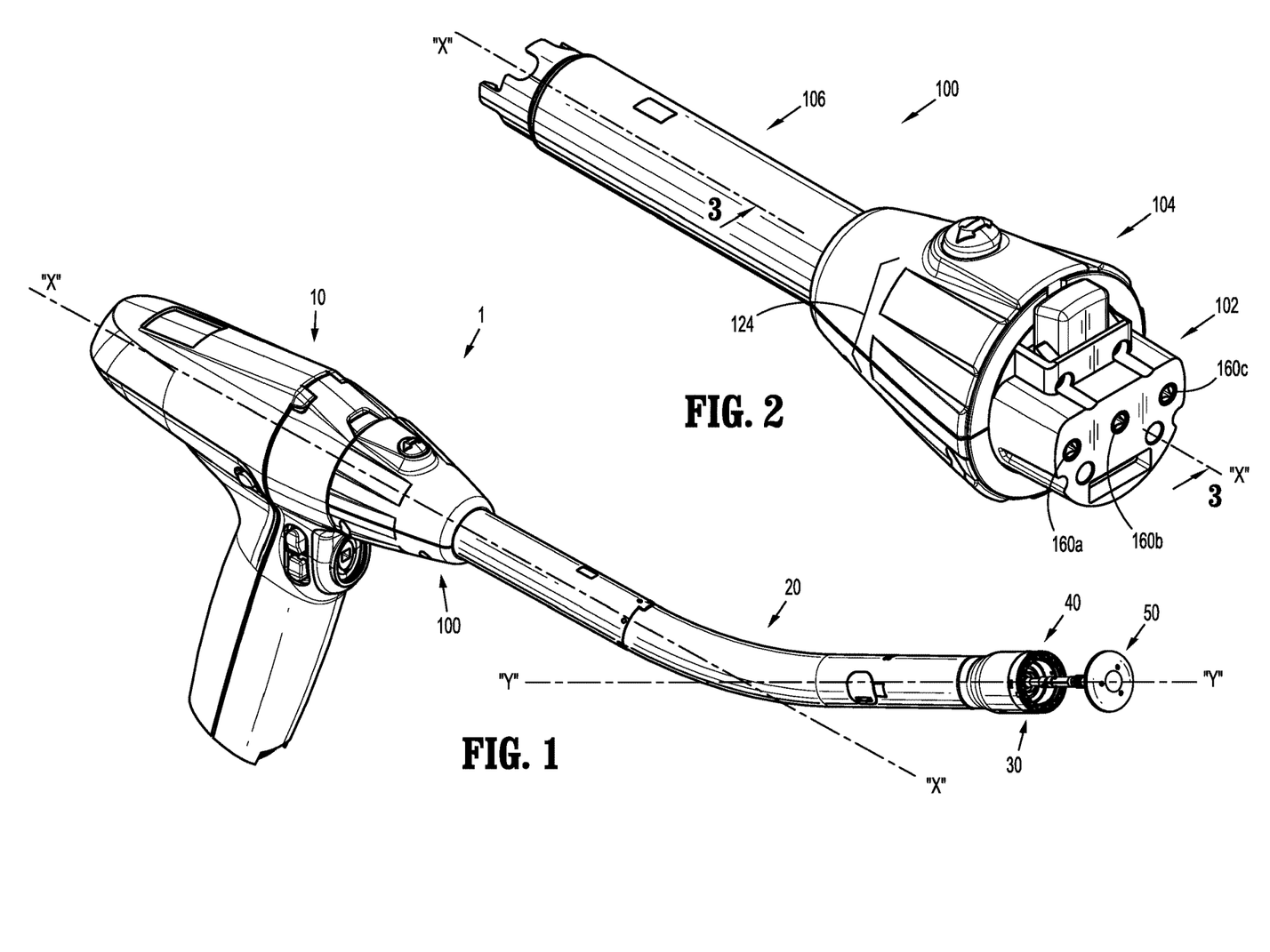
FIG. 1 is a perspective view of an electromechanical surgical device including an adapter assembly, in accordance with an embodiment of the present disclosure, an exemplary actuation assembly, an exemplary extension assembly, and an exemplary end effector.
FIG. 2 is a perspective view of the adapter assembly of FIG. 1.

With reference to FIGS. 1 and 2, an adapter assembly in accordance with an embodiment of the present disclosure, shown generally as adapter assembly 100, is a component of a powered handheld electromechanical instrument, shown generally surgical instrument 1. As illustrated in FIG. 1, the surgical instrument 1 includes an actuation assembly 10 configured for selective connection with the adapter assembly 100, and, in turn, the adapter assembly 100 is configured for selective connection with an extension assembly 20. The extension assembly 20 is configured for selective connection with a tool assembly or end effector, e.g. tool assembly 30, which may, in exemplary embodiments, include a loading unit 40 and an anvil assembly 50, for applying a circular array of staples (not shown) to tissue (not shown). For a detailed description of an exemplary actuation assembly, please refer to commonly owned U.S. Pat. No. 9,055,943, the content of which is incorporated by reference herein in its entirety.

Although the aspects of the present disclosure will be shown and described as relates to the adapter assembly 100, it is envisioned that the aspects of the present disclosure may be adapted for use with adapter assemblies having an alternative configuration. For a detailed description of exemplary adapter assemblies and exemplary extension assemblies, please refer to commonly owned U.S. patent application Ser. No. 14/875,766 ("the '766 application"), filed Oct. 6, 2015, the content of which is incorporated by reference herein in its entirety.

Figure 3:
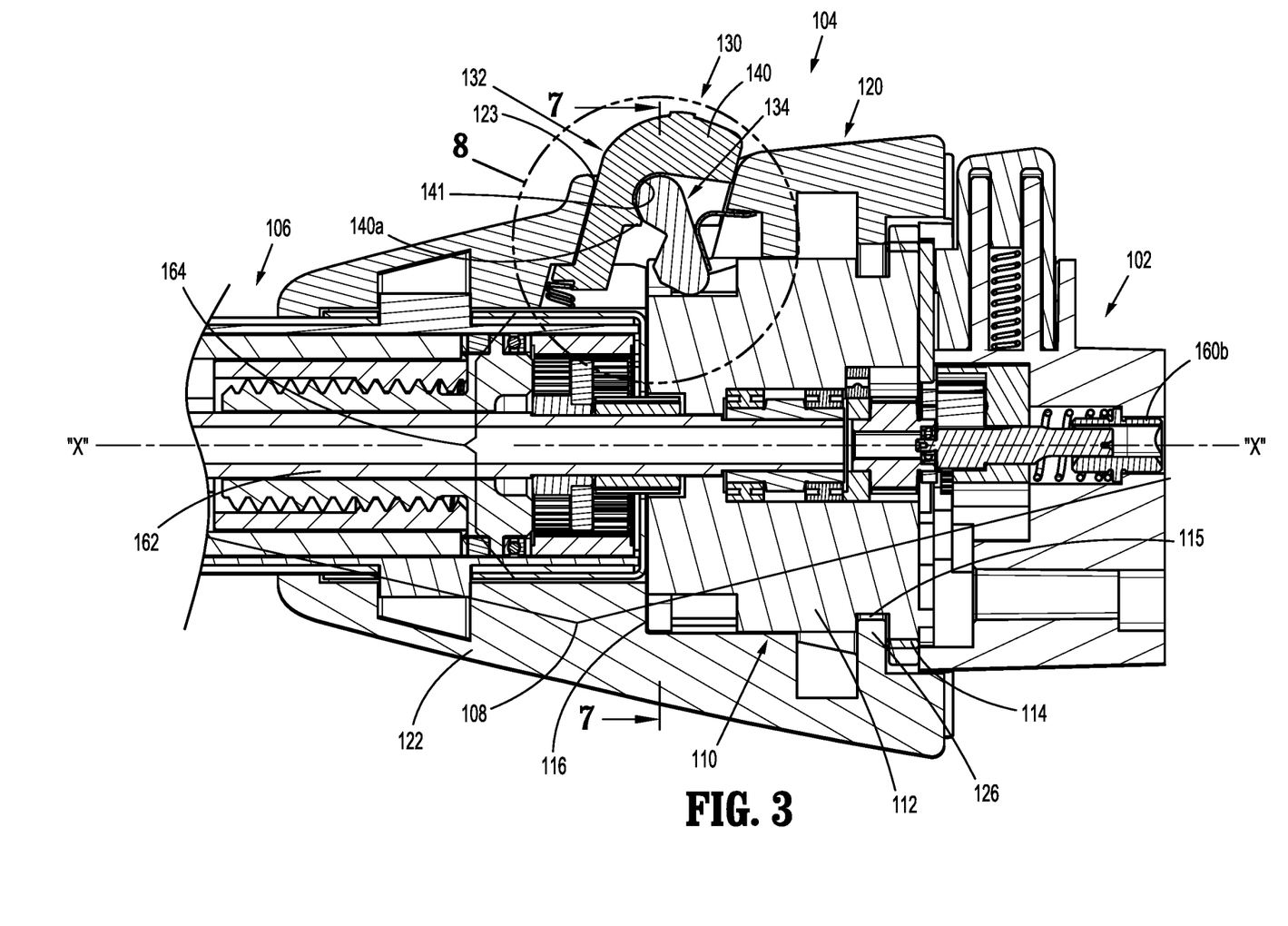
FIG. 3 is a cross-sectional side view of a handle assembly of the adapter assembly of FIG. 1 taken along line 3-3 of FIG. 2.

With reference now to FIGS. 2 and 3, the adapter assembly 100 includes a coupling assembly 102, a handle assembly 104 supported relative to the coupling assembly 102, an elongate body portion 106 extending distally from the handle assembly 104, and a drive assembly 108 (FIG. 3) extending through the coupling assembly 102, the handle assembly 104 and the elongate body portion 106. The coupling assembly 102 selectively secures the adapter assembly 100 to the actuation assembly 10 (FIG. 1). The drive assembly 108 extends through the coupling assembly 102, the handle assembly 104, and the elongate body portion 106 of the adapter assembly 100, and is configured for transferring power from the actuation assembly 10 (FIG. 1) to an attached end effector, i.e., tool assembly 30 (FIG. 1), for effecting actuation of the tool assembly 30.

With continued reference to FIGS. 2 and 3, briefly, the drive assembly 108 of the adapter assembly 100 includes first, second, and third connectors 160a, 160b, 160c (FIG. 2) configured for operable connection with first, second, and third drive members (not shown) of the actuation assembly 10. As shown in FIG. 3, the second connector 160b is operably connected to an elongate drive shaft 162 for transferring rotational motion through the adapter assembly 100. Each of the first and third connectors 160a, 160c are operably connected to planetary gear assemblies 164 (FIG. 3; only one shown) supported within the adapter assembly 100. The planetary gear assemblies 164 are configured to convert the rotational motion from the actuation assembly 10 to longitudinal motion. For a detailed description of exemplary adapter assemblies, including an exemplary coupling assembly and exemplary drive assemblies, please refer to the '766 application, the content of which was previously incorporated herein.

With particular reference now to FIG. 3, the handle assembly 104 of the adapter assembly 100 includes a base member or core 110, a rotation handle 120 rotatably supported on the base member 110, and a locking mechanism 130 operably supported on the rotation handle 120. As will be described in further detail below, when the locking mechanism 130 is in an unlocked configuration (FIGS. 9 and 10), the rotation handle 120 is rotatable along the longitudinal axis "x" relative to the base member 110, and when the locking mechanism 130 is in a locked configuration (FIGS. 7 and 8), the rotation handle 120 is rotationally secured relative to the base member 110. In particular, rotation of the rotation handle 120 about a longitudinal axis "x" of the adapter assembly 100 causes the end effector, i.e., tool assembly 30 (FIG. 1), which defines a longitudinal axis "y" (FIG. 1), to articulate or pivot with respect to the longitudinal axis "x" of the adapter assembly 100 to permit positioning of the tool assembly 30 relative to the actuation assembly 10. As such, a clinician is able to orient the tool assembly 30 relative to the actuation assembly 10 without changing the orientation of the actuation assembly 10.

Figure 4:
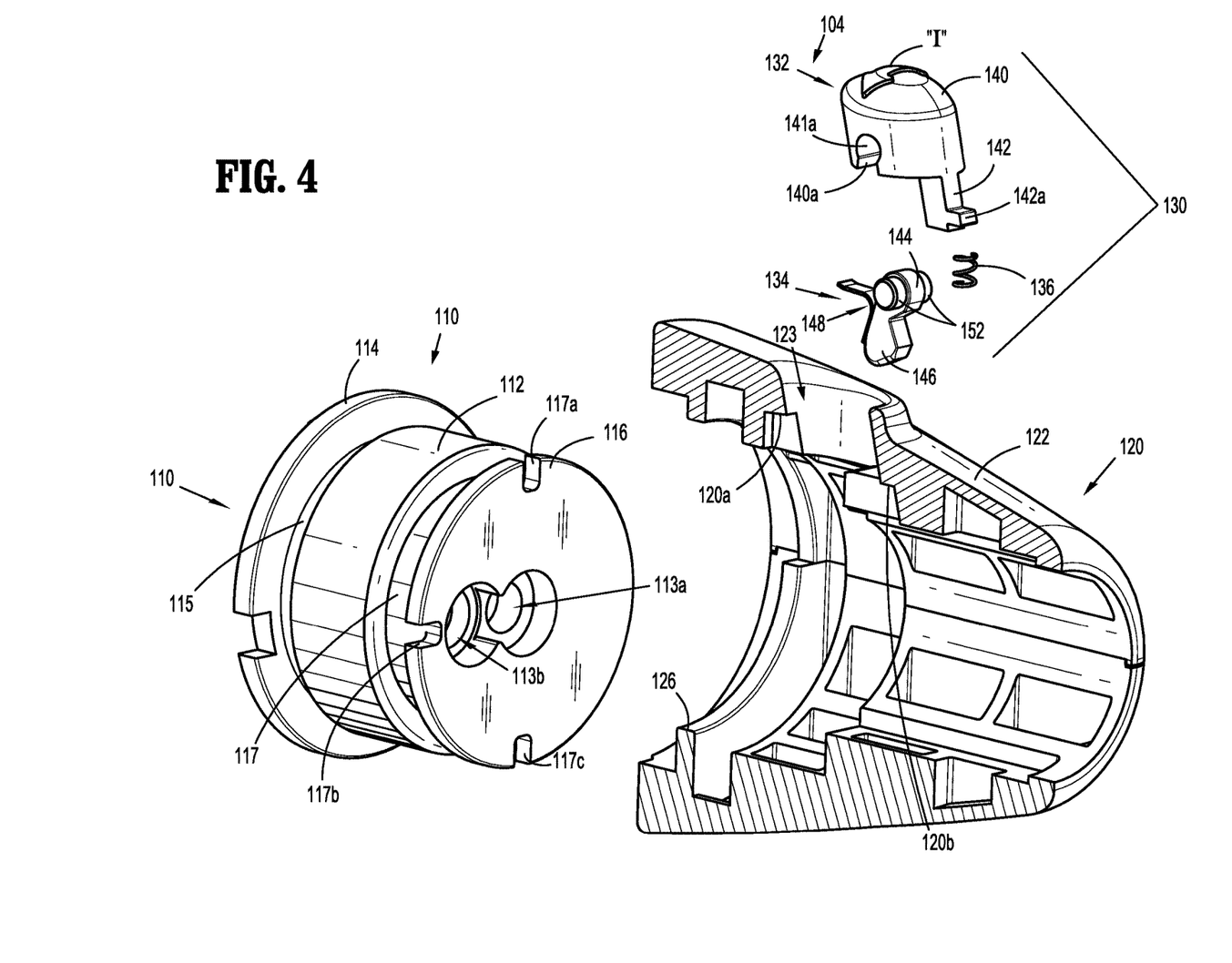
FIG. 4 is a perspective, partial cross-sectional side view of a base member and a rotation handle of the handle assembly of the adapter assembly of FIG. 1, with parts separated.

With additional reference to FIG. 4, the base member 110 includes a substantially cylindrical member 112 defining a pair of longitudinal openings 113a, 113b for receiving the drive assembly 108 (FIG. 3) therethrough. The base member 110 includes proximal and distal annular flanges 114, 116 and further defines proximal and distal annular grooves 115, 117. The proximal annular flange 114 facilitates attachment of the base member 110 of the handle assembly 104 to the coupling assembly 102. The proximal annular groove 115 accommodates an annular flange of 126 of the rotation handle 120 to rotatably secure the rotation handle 120 to the base member 110.

With reference still to FIGS. 3 and 4, the distal annular flange 116 and the distal annular groove 117 of the base member 110 operate in combination with the locking mechanism 130 of the handle assembly 104 to secure the rotation handle 120 in fixed rotational orientations relative to the base member 110. In particular, the distal annular flange 116 of the base member 110 defines first, second, and third radial cutouts 117a, 117b, 117c configured to selectively receive a lock portion 146 of a locking member 134 of the locking mechanism 130. Although shown with first and third cutouts 117a, 117c opposed to one another, and second cutout 117b oriented perpendicular to the first and third cutouts 117a, 117c, it is envisioned that the distal annular flange 116 may define any number of cutouts, and the cutouts may be arranged in any suitable configuration. For example, the cutouts may be arranged in set intervals, and, where the drive assembly 108 permits, the cutouts may be formed extending entirely around the distal annular flange 116 to permit locking of the rotation handle 120 in any three-hundred sixty degree (360°) orientation about the base member 110.

With continued reference to FIGS. 3 and 4, the rotation handle 120 includes a frustoconical body 122 having a plurality of ridges 124 (FIG. 1) configured for operable engagement by a user. The elongate body portion 106 (FIG. 2) is secured to the rotation handle 120 such that rotation of the rotation handle 120 about the longitudinal axis "x" of the adapter assembly 100 causes rotation of the elongate body portion 106 about the longitudinal axis "x". In this manner, an end effector, e.g. tool assembly 30 (FIG. 1), secured to the elongated body portion 120 of the adapter assembly 100, or an end effector secured to an extension assembly, e.g., extension assembly 20 (FIG. 1), which is secured to the elongated body portion 120 of the adapter assembly 100, is rotatable independent of movement of the actuation assembly 10 (FIG. 1) to which the adapter assembly 100 is attached.

As noted above, the rotation handle 120 includes an annular flange 126 (FIG. which is received within the proximal annular groove 115 of the base member 110 to permit rotation of the rotation handle 120 relative to the base member 110. The rotation handle 120 defines a radial opening 123 for operably receiving the locking mechanism 130. The opening 123 in the rotation handle 120 is positioned in alignment or registration with the distal annular groove 117 of the base member 110 such that the locking member 134 of the locking mechanism 130 is receivable with the distal annular groove 117 and selectively receivable within each of the first, second, and third cutouts 117a, 117b, 117c in the distal annular flange 116.

Figure 5:
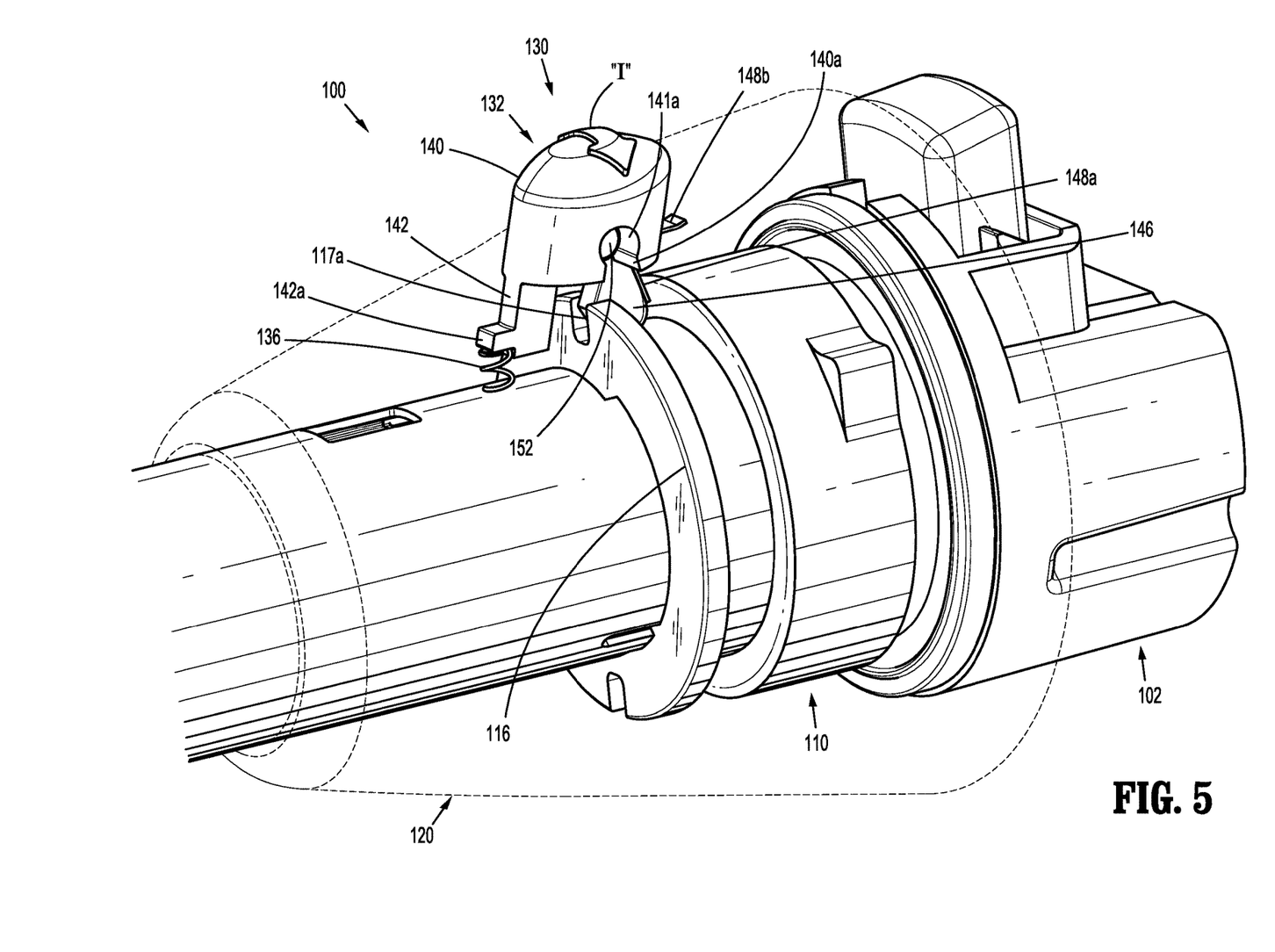
FIG. 5 is a perspective side view of a locking mechanism of the handle assembly of the adapter assembly of FIG. 1, with the rotation handle shown in phantom.
Figure 6:
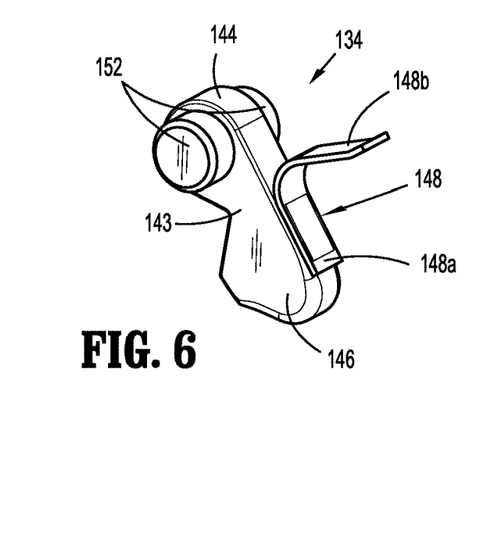
FIG. 6 is a perspective side view of a locking member of the locking mechanism of FIG. 5.

With additional reference to FIGS. 5 and 6, the locking mechanism 130 of the handle assembly 104 of the adapter assembly 100 includes a button or latch member 132 for disengaging the locking mechanism 130. The locking mechanism 130 further includes the locking member 134 disposed within the rotation handle 120 and pivotal relative to the button member 132. A first spring member, e.g., compression spring 136, biases the locking member 134 to a locked configuration (FIG. 5).

With continued reference to FIGS. 4 and 5, the button member 132 of the locking mechanism 130 includes a base portion 140 configured for operable engagement by a user, and a flange 142 extending from the base portion 140 for engaging the first spring member 136. The base portion 140 of the button member 132 may include indicia for indicating to a user, for example, a direction of rotation of the rotation handle 120. As shown, the base portion 140 of the button member 132 includes a double-sided arrow "I", indicating that the handle assembly 104 is rotatable about the longitudinal axis "x".

The button member 132 of the locking mechanism 130 defines a recess 141 (FIG. 3) for receiving the locking member 134, and a pair of cylindrical openings 141a formed outwardly of the recess for pivotally receiving the pivot members 152 of the locking member 134. A lip 140a extends along the cylindrical openings 141a for pivotally maintaining the locking member 134 relative to the button member 132. The flange 142 includes a protrusion 142a configured to engage a surface 120a of the rotation handle 120 to maintain the button member 132 within the opening 123 in the rotation handle 120. The protrusion 142a also engages the first spring member 136 of the locking mechanism 130. In particular, the first spring member 136 biases the button member 132 of the locking mechanism 130 in a radially outward direction.

With additional reference to FIG. 6, the locking member 134 of the locking mechanism 130 includes a pivot portion 144 and a lock portion 146. The pivot members 152 of the locking member 134 extend outwardly from the pivot portion 144 and are configured to be received within the cylindrical openings 141a in the button member 132 of the locking mechanism 130. The lock portion 146 of the locking member 134 is configured to be selectively received within the first, second, and third radial cutouts 117a, 117b, 117c in the distal annular flange 116 of the base member 110. A notch 143 is formed between the pivot portion 144 and the lock portion 146 of the locking member 134. As will be described in further detail below, alignment of the notch 143 with the distal annular flange 116 of the base portion 110 when the locking mechanism 130 is in in unlocked position permits the rotation handle 120 to rotate relative to the base member 110.

A second spring member, e.g., leaf spring 148, is secured relative to the locking member 134 and engages a second surface 120b of the rotation handle 120. As will be described in further detail below, the second spring member 148 returns the locking member 134 to a locked position (FIG. 3) following release of the button member 132 of the locking mechanism 130.

Figure 7:
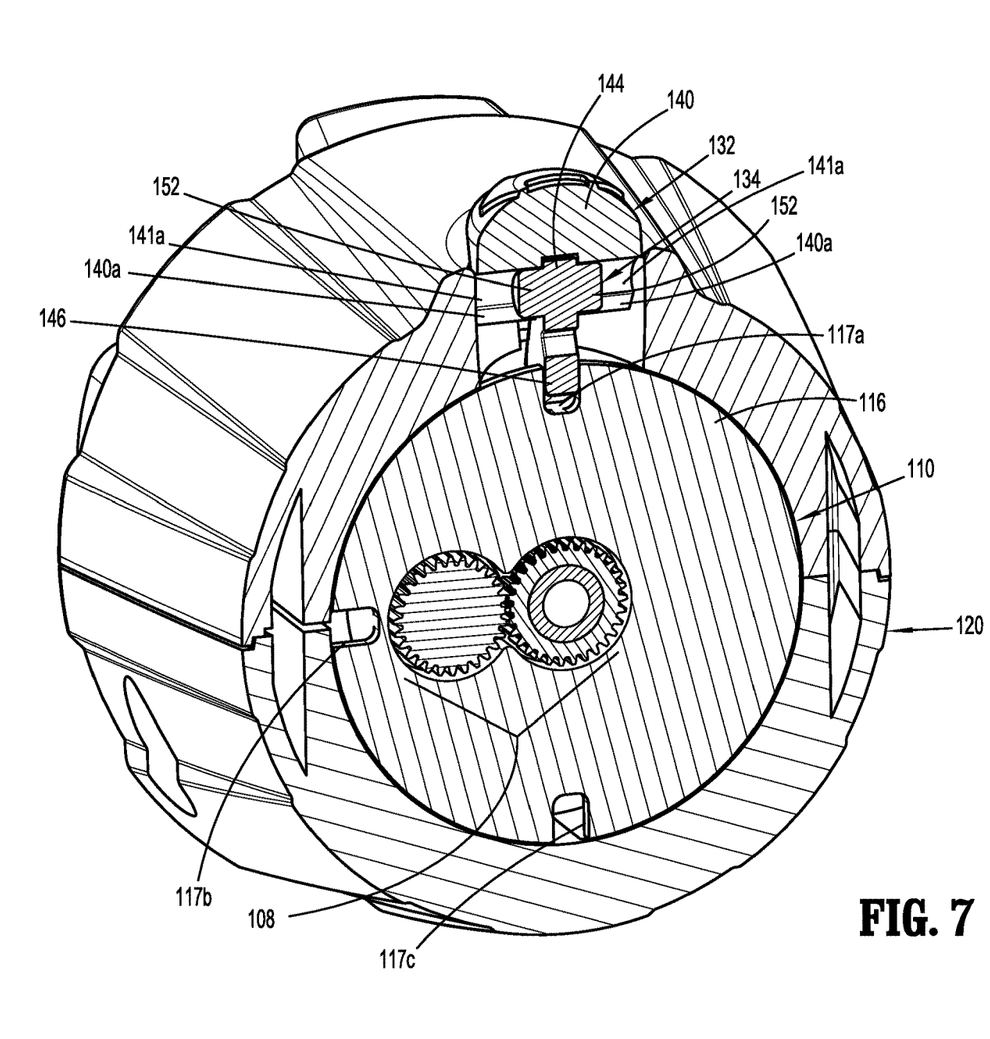
FIG. 7 is a cross-sectional end view of the adapter assembly of FIG. 1 taken along line 7-7 of FIG. 3, with the locking mechanism in a first or locked position.
Figure 8:
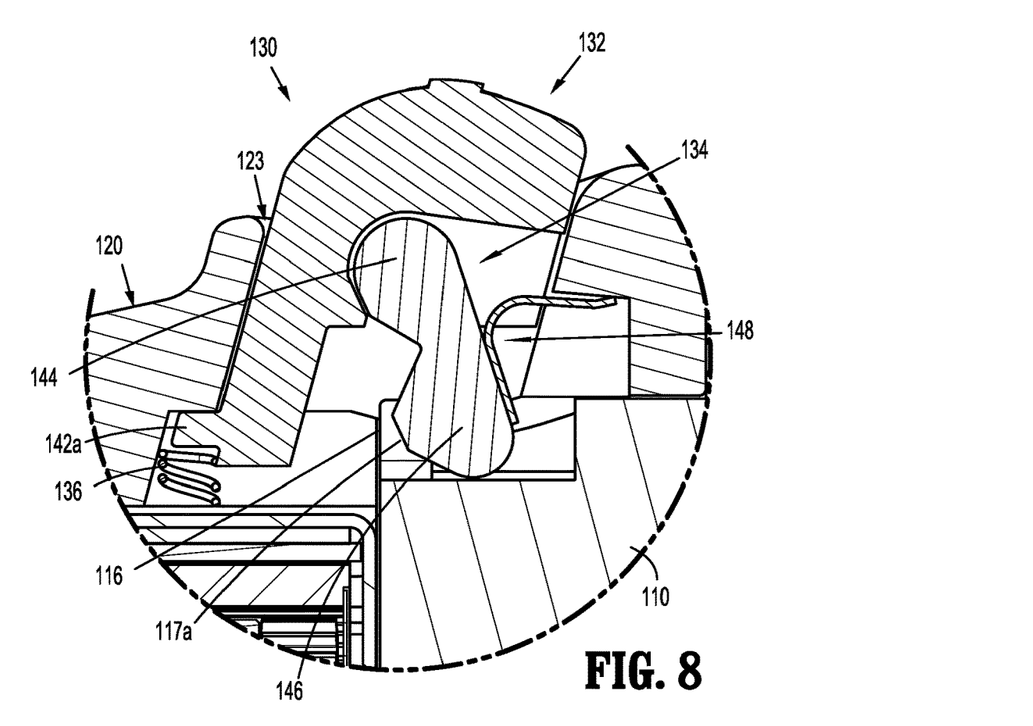
FIG. 8 is an enlarged view of the indicated area of detail in FIG. 3, with the locking mechanism in the first position.

The operation of the locking mechanism 130 will now be described with reference to FIGS. 7-11. Referring initially to FIGS. 7 and 8, the locking mechanism 130 is shown in the locked configuration. In particular, the lock portion 146 of the locking member 134 is received within the first cutout 117a in the distal annular flange 116 of the base member 110. In the locked configuration, the button member 132 of the locking mechanism 130 is biased radially outward by spring member 136. As noted above, the button member 132 is retained within the opening 123 of the rotation handle 120 by protrusion 142a extending from the flange 142 of the button member 132.

Figure 9:
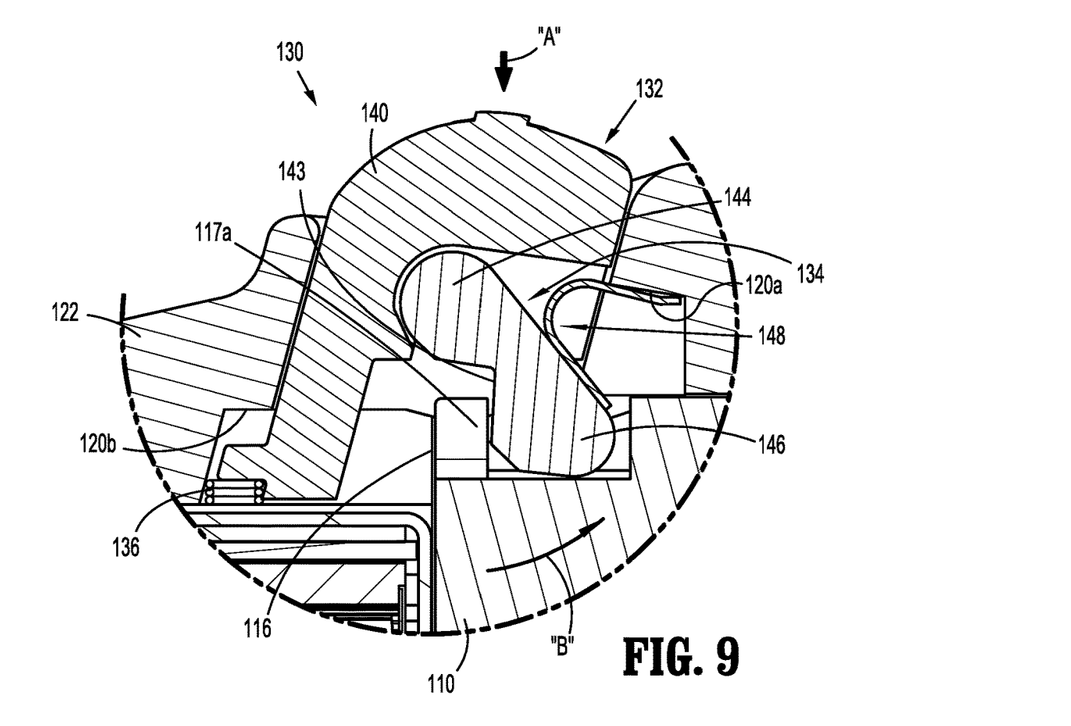
FIG. 9 is an enlarged view of the indicated area of detail in FIG. 3, with the locking mechanism in a second or unlocked position.
Figure 10:
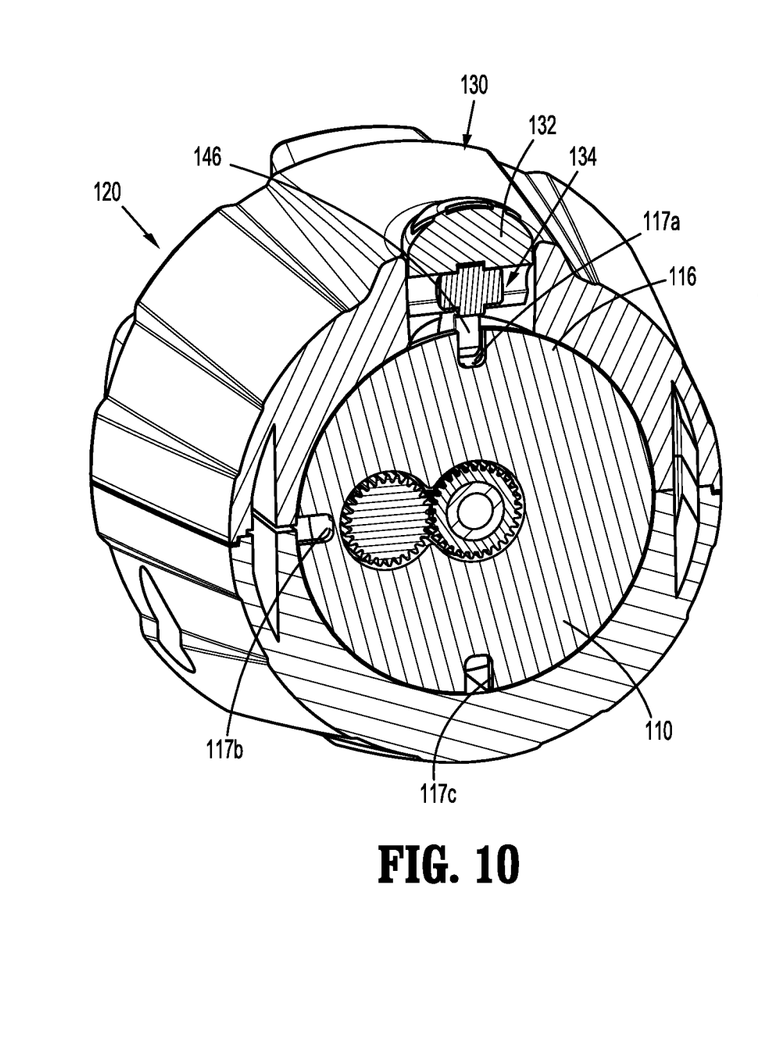
FIG. 10 is a cross-sectional end view of the adapter assembly of FIG. 1 taken along line 7-7 of FIG. 3, with the locking mechanism in the second position.

With reference now to FIGS. 9 and 10, when the button member 132 of the locking mechanism 130 is depressed, as indicated by arrow "A" in FIG. 9, the button member 132 moves radially inward against the bias of the spring member 136. As the button member 132 moves radially inward, the locking member 134 pivots about pivot members 152 (FIG. 6) in a counter-clockwise direction, as indicated by arrow "B" in FIG. 9, against the bias of the leaf spring 148. The counter-clockwise pivoting of the locking member 134 moves the locking portion 146 of the locking member 134 from within the first radial cutout 117a of the distal annular flange 116 of the base member 110, such that the notch 143 between the pivot portion 144 and lock portion 146 of the lock member 134 aligns with the distal annular flange 116.

Figure 11:
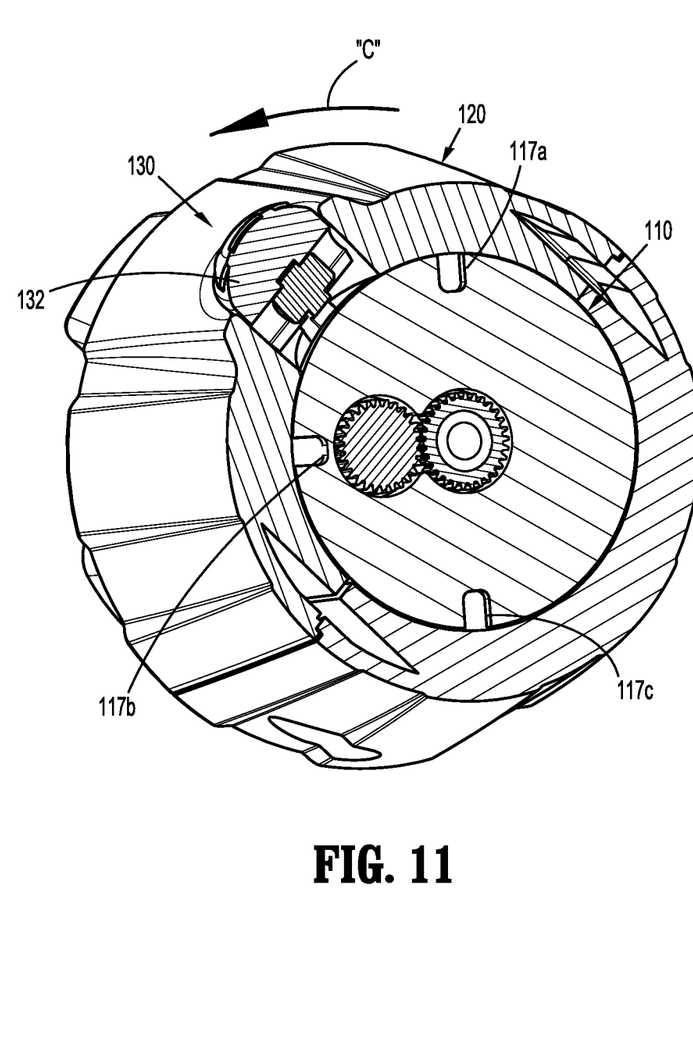
FIG. 11 is a cross-sectional end view of the adapter assembly of FIG. 1 taken along line 7-7 of FIG. 3, with the handle assembly rotated in a counter-clockwise direction.

Turning now to FIG. 11, once the locking mechanism 130 is in the unlocked configuration, the rotation handle 120 may be rotated relative to the base member 120, as indicated by arrow "C". The release of the button member 132 allows the spring member 136 to bias the button member 132 to its initial position. Similarly, leaf spring 148 biases the lock member 134 to its initial position. When the locking member 134 is aligned with one of the first, second, and third radial cutouts 117a, 117b, 117c of the distal annular flange 116 of the base member 110, receipt of the lock portion 146 of the lock member 134 within the respective first, second, and third cutout 117a, 117b, 117c rotationally locks the rotation handle 120 relative to the base member 110.

The locking mechanism 130 may be used throughout the surgical procedure to rotate the elongate body portion 106 of the adapter assembly 100 relative to the actuation assembly 10 (FIG. 1). Following a surgical procedure, the adapter assembly 100 may be sterilized and reused.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to an actuation assembly, the adapter assembly comprising:
   a base member configured for operable connection to an actuation assembly and defining a plurality of notches spaced at least partially about a circumference of the base member;
   a handle assembly supported on the base member and rotatable about a longitudinal axis of the base member; and
   a latch mechanism supported on the handle assembly, the latch mechanism including a button member and a locking member pivotally secured to the button member, wherein the button member is movable between an initial position and a depressed position to move the locking member from a first position in which the locking member is received within one of the plurality of notches to rotationally lock the handle assembly relative to the base member, to a second position in which the locking member is spaced from the plurality of notches to permit rotation of the handle assembly relative to the base member.

2. The adapter assembly of claim 1, wherein the base member includes a distal annular flange extending at least partially about the circumference of the base member and defining the plurality of notches.

3. The adapter assembly of claim 2, wherein the locking member defines a notch that aligns with the distal annular flange when the locking member is in the second position.

4. The adapter assembly of claim 1, wherein the plurality of notches are spaced at regular intervals about the circumference of the base member.

5. The adapter assembly of claim 1, wherein the button member is positioned on a radially outer surface of the handle assembly.

6. The adapter assembly of claim 1, wherein the latch mechanism includes a biasing member for biasing the button member radially outward.

7. The adapter assembly of claim 6, wherein the biasing member is a compression spring.

8. The adapter assembly of claim 1, wherein the plurality of notches includes a first notch and a second notch disposed one-hundred eighty degrees (180°) opposite the first notch.

9. The adapter assembly of claim 8, wherein the plurality of notches includes a third notch disposed between the first and second notches.

10. The adapter assembly of claim 9, wherein the third notch is disposed ninety degrees (90°) relative to the first notch.

11. The adapter assembly of claim 1, wherein the latch mechanism includes a biasing member for biasing the locking member.

12. The adapter assembly of claim 11, wherein the biasing member is a leaf spring.

13. The adapter assembly of claim 1, wherein the button member includes indicia for indicating the direction of rotation of the handle assembly relative to the base member.

14. The adapter assembly of claim 1, wherein the base member is rotationally fixed relative to the actuation assembly when the adapter assembly is operably connected to the actuation assembly.

15. An adapter assembly for operably connecting an end effector to an actuation assembly, the adapter assembly comprising:
   a base member configured for operable connection to an actuation assembly and defining a plurality of notches spaced at least partially about a circumference of the base member;
   a handle assembly supported on the base member and rotatable about a longitudinal axis of the base member; and
   a latch mechanism supported on the handle assembly, the latch mechanism including a button member and a locking member pivotally secured to the button member, wherein the button member is movable to move the locking member from a first position in which the locking member is received within one of the plurality of notches to rotationally lock the handle assembly relative to the base member, to a second position in which the locking member is spaced from the plurality of notches to permit rotation of the handle assembly relative to the base member.

16. The adapter assembly of claim 15, wherein the button member is movable between an initial position and a depressed position.

17. The adapter assembly of claim 15, wherein handle assembly defines an opening, the button member being disposed within the opening in the handle assembly.

18. The adapter assembly of claim 15, wherein the base member includes a distal annular flange extending at least partially about the circumference of the base member and defining the plurality of notches.

19. The adapter assembly of claim 18, wherein the locking member defines a notch that aligns with the distal annular flange when the locking member is in the second position.

20. The adapter assembly of claim 15, wherein the latch mechanism includes a first biasing member for biasing the button member radially outward and a second biasing member for biasing the locking member.

* * * * *